United States Patent
Di Emidio

(10) Patent No.: US 6,878,152 B2
(45) Date of Patent: Apr. 12, 2005

(54) FORCEPS USED FOR THE SURGICAL REDUCTION OF FRACTURED FACIAL BONES

(75) Inventor: Paolo Di Emidio, Controguerra (IT)

(73) Assignee: Piergiacomi SUD- S.R.L., Monteprandone (IT)

( * ) Notice: Subject to any disclaimer, the term of this patent is extended or adjusted under 35 U.S.C. 154(b) by 399 days.

(21) Appl. No.: 10/035,054

(22) Filed: Dec. 28, 2001

(65) Prior Publication Data

US 2003/0009192 A1 Jan. 9, 2003

(30) Foreign Application Priority Data

Jul. 3, 2001 (IT) .................................. MC2001A0072

(51) Int. Cl.$^7$ .............................................. A61B 17/08
(52) U.S. Cl. ...................................... 606/151; 433/205
(58) Field of Search ................................ 606/157, 158, 606/151; 433/205; 24/551, 547, 53

(56) References Cited

U.S. PATENT DOCUMENTS

| | | | | | |
|---|---|---|---|---|---|
| 26,975 | A | * | 1/1860 | Evans | 251/231 |
| 180,430 | A | * | 8/1876 | Lambert | 24/551 |
| 356,665 | A | * | 1/1887 | Seymour | 24/551 |
| 878,727 | A | * | 2/1908 | Harris et al. | 24/533 |
| 1,058,257 | A | * | 4/1913 | Perry et al. | 24/533 |
| 1,222,510 | A | * | 4/1917 | Zirkle | 24/551 |
| 1,253,468 | A | * | 1/1918 | Cockrill | 24/551 |
| 1,380,534 | A | * | 6/1921 | Lloyd | 211/49.1 |
| 1,564,323 | A | * | 12/1925 | Chamandy | 40/649 |
| 2,007,612 | A | * | 7/1935 | Perkins | 281/43 |
| 2,810,176 | A | * | 10/1957 | Gaafar | 24/551 |
| 4,657,457 | A | * | 4/1987 | Rickwood | 411/93 |
| 5,053,045 | A | * | 10/1991 | Schmidt et al. | 606/157 |
| 5,569,274 | A | * | 10/1996 | Rapacki et al. | 606/158 |
| 5,792,149 | A | * | 8/1998 | Sherts et al. | 606/142 |
| 6,616,686 | B1 | * | 9/2003 | Coleman et al. | 606/219 |

FOREIGN PATENT DOCUMENTS

EP 0 386 361 A1 * 12/1990 ........... A61B/17/08

* cited by examiner

*Primary Examiner*—Anhtuan T. Nguyen
*Assistant Examiner*—Bradford C Pantuck
(74) *Attorney, Agent, or Firm*—Armstrong, Kratz, Quintos, Hanson & Brooks, LLP

(57) ABSTRACT

The present invention relates to a forceps used for the surgical reduction of facial bones, characterized by the fact that it comprises two shaped branches diverging from opposite sides starting from a central elastic loop. Each branch develops on three Cartesian axis and has a first rectilinear section joined to a second section with 90° orientation, laying on the same plane that contains the loop and joined in turn with a 90° ending section, whose end is slightly bent towards the central loop.

2 Claims, 1 Drawing Sheet

FORCEPS USED FOR THE SURGICAL REDUCTION OF FRACTURED FACIAL BONES

CROSS REFERENCE TO RELATED APPLICATIONS

"This application claims priority from Italian Patent Application MC2001 A 000072 which was filed on Jul. 3, 2001."

STATEMENT REGARDING FEDERALLY SPONSORED RESEARCH OR DEVELOPMENT (Not Applicable)

INCORPORATION-BY-REFERENCE OF MATERIAL SUBMITTED ON A COMPACTDISC (Not Applicable)

REFERENCE TO A MICROFICHE APPENDIX SPECIFYING THE TOTAL NUMBER OF MICROFICHE AND TOTAL NUMBER OF FRAMES (Not Applicable)

BACKGROUND OF THE INVENTION

1. Field of the Invention

The present patent application relates to a forceps used for the surgical reduction of fractured facial bones.

2. Description of Related Art

Osteosynthesis systems are frequently used in maxillofacial traumatology and orthopaedic surgery of maxillary bones, since they guarantee the perfect stability of stumps or fractured bone fragments. In particular, the use of metal plates to be fixed to stumps or fractured bone fragments with surgical screws is very diffused.

As a matter of fact, these plates are considered as the most suitable containment instruments to ensure the stability of bone fragments, which is an essential condition for the formation of callus.

Before fixing the surgical plates, however, it is necessary to carry out the surgical reduction of fractured bone segments, in order to restore their continuity.

Only after reduction the bone segments will be able to consolidate correctly from the physiological and functional viewpoint through the use of metal plates.

It must be noted that the instruments that are currently used for the surgical reduction of facial bone segments cannot be considered as fully satisfactory. Although they guarantee good functional efficiency, they are impaired by the fact that they require extremely long surgical time.

In particular, these instruments are represented by the so-called "metal splints" designed for application on dental arches as reduction-containment means.

This consolidated technology provides for the application of metal arches joined with metal wires to each tooth on dental arches. Reduction is therefore obtained by applying elastic traction or a block with metal wires between two metal arches (the aforementioned splints).

This allows for obtaining the reduction of fractured segments and, in mandibular fractures, a dental articulation (occlusion) compatible with the pre-existing anatomy.

As mentioned earlier, the execution of this technology on patients is an extremely long operation, and it takes approximately $3\%_0$ minutes: firstly, the splints must be installed and then removed from the patient's mouth, after fixing the metal plates to the bone segments.

BRIEF SUMMARY OF THE INVENTION

The purpose of the present invention is to develop an alternative technology to the use of traditional metal splints. In this perspective the artifact according to the present invention has been developed, which is capable of ensuring the same reduction-containment as the splints, while allowing for simpler and faster installation.

More precisely, the new artifact consists in an elastic forceps with simple structure made of suitable shaped metal rod.

Apart from easy assembling, the new forceps provides good visibility of the surgical field and ensures the ergonomics of the surgical intervention.

Another advantage of the artifact according to the present invention is represented by indefinite duration, since it can be repeatedly used, after sterilisation in autoclave

BRIEF DESCRIPTION OF SEVERAL VIEWS OF THE DRAWINGS

For major clarity the description of the present invention continues with reference to the enclosed drawing, which is intended for purposes of illustration and not in a limiting sense, whereby.

DETAILED DESCRIPTION OF THE INVENTION

Figures 1, 2, 3:
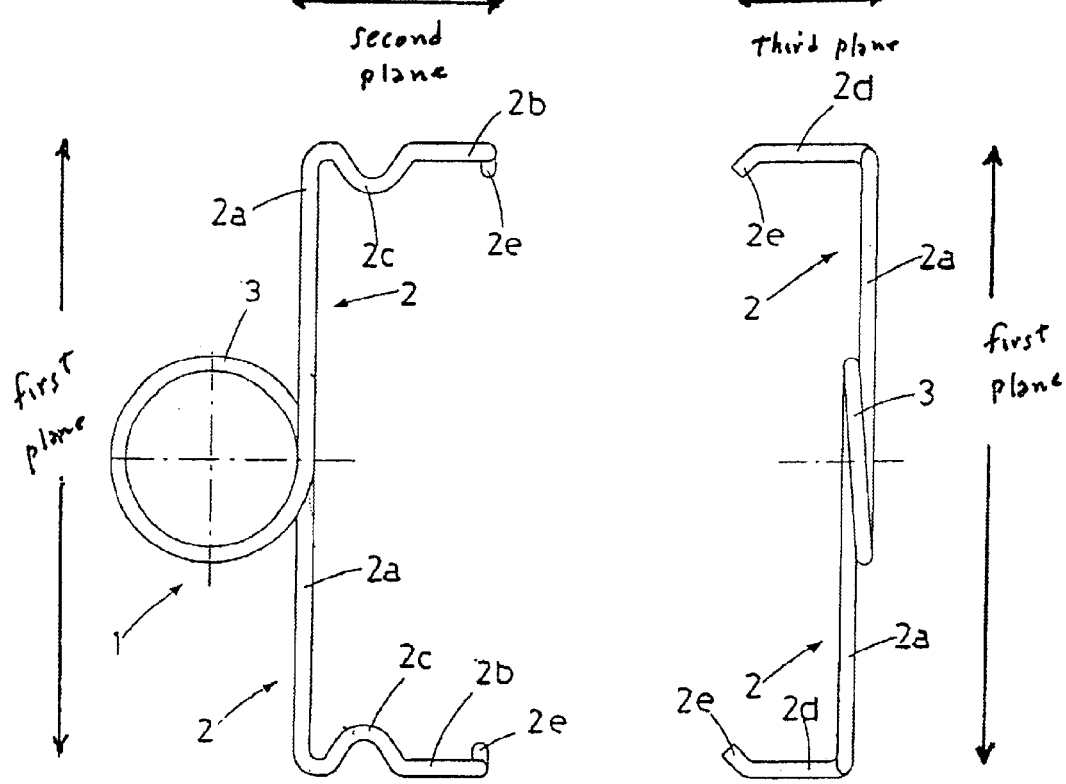
FIG. 1 is a side view of the forceps according to the present invention.
FIG. 2 is a top view of FIG. 1; Image Page 3
FIG. 3 is an axonometric representation of the application of two forceps on a human skull.

The forceps (I) according to the present invention comprises shaped branches (2) diverging from opposite sides starting from a central elastic loop (3).

Each branch (2) develops on three Cartesian axis and has a first rectilinear section (2a) joined to a second section with 90° orientation (2b) laying on the same plane that contains the loop (3); it being provided that the second section (2b) has a groove (2c).

The second section (2b) of each branch (2) is in turn joined with a 90° ending section (2d), whose end (2e) is slightly bent towards the central loop (3).

The two bent ends (2e) of the branches (2a) of the forceps (1) are designed to be inserted and held into suitable holes previously drilled on the bone segments to be reduced, as shown in FIG. 3.

In particular, the holes designed to act as connection points for the bent ends (2e) of the branches (2) are drilled on bone segments with a distance slightly higher than the distance between the bent ends (2e) when the forceps (1) is in idle state.

This allows for "stretching" the elastic structure of the forceps (1) when the forceps (1) is hooked to the holes, in order to guarantee stable fixing and most of all to hold firmly the bone segments one against the other.

The grooves (2c) on the branches (2) of the forceps (1) are designed to act as housings for a wire used to ensure stable fixing of the branches (2) in order to prevent the risk of accidental divarication of the branches (2), thus releasing the entire forceps (1) from its operational position.

What is claimed is:

1. A surgical forceps used for the surgical reduction of fractured facial bones, the surgical forceps adapted to being received in holes in bone segments on opposite sides of the mouth, characterised by the fact that it comprises two shaped branches (2) each branch diverging from opposite sites starting from a respective central elastic loop (3) encircling 360° being in first plane, with each branch developing on a Cartesian coordinate system and having a first rectilinear section (2a) joined to a second section (2b) with 90° orientation therebetween, the second section being in a second plane with respect to the loop (3) and each branch joined at an angle of 90° with respect to a respective ending section (2d) the respective ending sections being in a third plane perpendicular to the first and second planes, each ending section having an end (2e) oriented in a first direction and slightly bent towards the central loop (3) such that the slightly bent ends are received in the holes in the bone segments.

2. A surgical forceps according to claim 1, characterised by the fact that the second section (2b) of each branch (2) is provided with a groove (2c), the groove (2c) being an arcuate bend in the planar second section (2b).

* * * * *